(12) United States Patent
Gosalvez Berenguer et al.

(10) Patent No.: US 9,212,391 B2
(45) Date of Patent: *Dec. 15, 2015

(54) METHOD FOR DETERMINING DNA FRAGMENTATION IN MICROORGANISMS

(71) Applicant: Universidad Autonoma de Madrid, Madrid (ES)

(72) Inventors: Jaime Gosalvez Berenguer, Madrid (ES); Jose Luis Fernandez Garcia, Madrid (ES); Vicente Goyanes Villaescusa, Madrid (ES); German Bau Arevalo, Madrid (ES); Lourdes Muriel Rios, Madrid (ES); Monica Cartelle Gestal, Madrid (ES)

(73) Assignee: UNIVERSIDAD AUTONOMA DE MADRID, Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/949,047

(22) Filed: Jul. 23, 2013

(65) Prior Publication Data

US 2014/0024031 A1    Jan. 23, 2014

Related U.S. Application Data

(63) Continuation of application No. 12/513,560, filed as application No. PCT/ES2007/000637 on Nov. 8, 2007, now Pat. No. 8,492,086.

(30) Foreign Application Priority Data

Nov. 10, 2006    (ES) .................................. 200602859

(51) Int. Cl.
*C12Q 1/68* (2006.01)
*C07H 21/00* (2006.01)
*C12N 15/10* (2006.01)

(52) U.S. Cl.
CPC .......... *C12Q 1/6841* (2013.01); *C12N 15/1003* (2013.01)

(58) Field of Classification Search
CPC ........ C12Q 1/68; C12Q 1/6834; C07H 21/00; C12N 15/00; C12N 15/1006
USPC .......................................... 435/6.1; 536/22.1
See application file for complete search history.

(56) References Cited

U.S. PATENT DOCUMENTS 8,492,086 B2 * 7/2013 Berenguer et al. ............. 435/6.1
2006/0035253 A1   2/2006 Sayer et al.

FOREIGN PATENT DOCUMENTS

| EP | 1 710 320 | 10/2006 |
|----|-----------|---------|
| EP | 2 080 811 | 7/2009 |
| GB | 2128737 A | 5/1984 |
| WO | 02055015 A2 | 7/2002 |
| WO | 03048380 A1 | 6/2003 |
| WO | 2006079864 A1 | 8/2006 |
| WO | 2008056016 A1 | 5/2008 |

OTHER PUBLICATIONS

Ahern H., Biochemical, Reagent Kits Offer Scientists Good return on Investment. The Scientist 9(15) : 20 (1995).*
Fernandez et al., 453 : 77-82 (2000).*
Singh et al. [Mutation Research 429:159-168 (1999)].*
Singh et al., A simple technique for quantitation of low levels of DNA damage in individual cells. Experimental Cell Research 175 (1) : 184-191 (1988).*
EP Office Action dated Dec. 19, 2013, issued in related EP Application No. 07823042.2 (4 pp).
Didenko, Vladimir V., ed. "In situ detection of DNA damage", Humana Press, 2002 (2 pp).
Enciso, M., et al., "A new method to analyze boar sperm DNA fragmentation under bright-field or fluorescence microscopy" Theriogenology 2006; vol. 65, Issue 2:308-316.
Fernandez, J.L. et al.,"DNA Breakage Detection-Fluorescence in Situ Hybridization (DBD-Fish)" 1998; 2000.
Erbes, Monika, et al. "Detection of primary DNA damage in Chlamydomonas reinhardtii by means of modified microgel electrophoresis", Environmental and Molecular Mutagenesis, vol. 30, Issue 4, pp. 448-458, 1997.
Fernandez, J.L. et al., "Application of FISH to detect DNA damage: DNA Breakage Detection-FISH (DBD-FISH)" Methods Mol Biol 2002; 203: 203-216.
Fernandez, J.L. et al.,"DNA Breakage Detection-FISH (DBD-FISH)", In: Rautenstrauss B, Liehr T, eds. FISH technology—Springer lab manual. Heidelberg: Springer-Verlag; 2002; 282-290.
Fernandez, J.L. et al., "DNA breakage detection-FISH (DBD-FISH) in human spermatozoa: technical variants evidence different structural features" Mutat Res 2000; 453:77-82.
Fernandez, J.L. et al., "Application of FISH for in situ detection and quantification of DNA breakage", Cytogenetics Cell Genetics,1998; 82:251-256.
Gosalvez, et al., "FISHing in the microwave: the easy way to preserve proteins. I. Colocalization of DNA probes and surface antigens in human leukocytes", Chromosome Research, 2002, vol. 10, Issue 2, pp. 137-143.
Harrison, Susan, T. L., "Bacterial cell disruption: A key unit operation in the recovery of intracellular products", Biotech ADA 1991: 9:217-240.
Kaldalu, N., et al., "Killing by Ampicillin and Ofloxacin Induces Overlapping Changes in *Escherichia coli* Transcription Profile", Antimicrob Agents Chemother 2004; 48:890-896.
Lecoeur, H., "Nuclear Apoptosis Detection by Flow Cytometry: Influence of Endogenous Endonucleases" Exp Cell Res 2002; 277:1-14.

(Continued)

*Primary Examiner* — Ethan C Whisenant
(74) *Attorney, Agent, or Firm* — Craig R. Miles; CR MILES P.C.

(57) ABSTRACT

The present invention relates to a process for determining the DNA integrity in microorganisms and a kit for evaluating the DNA integrity therein. Due to the fact that cell death means DNA fragmentation, with the present process the DNA fragmentation levels in microorganisms can be clearly discriminated in a simple, quick and accurate manner.

17 Claims, 10 Drawing Sheets

(56) References Cited

OTHER PUBLICATIONS

Lewis, Kim, "Programmed Death in Bacteria", Microbial and Mol. Biol. Rev., 2000; 64: 503-514.

Ligozzi, M., et al., "Isolation of total DNA from bacteria and yeast", Afr J Biotech 2003; 2: 251-253.

Maassen, C.B.M., "A rapid and safe plasmid isolation method for efficient engineering of recombinant lactobacilli expressing immunogenic or tolerogenic epitopes for oral administration", J Immunol Method 1090; 223: 131-136.

Niwa, T., "Lytic enzyme, labiase for a broad range of Gram-positive bacteria and its application to analyze functional DNA/RNA", J, Microbial Methods 2005; 61:251-260.

Olive, P.L., et al., "Heterogeneity in DNA damage using the comet assay", Cytometry Part A, 2005; 66:143.

Rodriguez, S., et al., "Critically short telomeres are associated with sperm DNA fragmentation ", Fertil Steril 2005; 84: 843-845.

Rohwer, F. et al., "Detection of DNA Damage in Prokaryotes by Terminal Deoxyribonucleotide Transferase-Mediated dUTP Nick End Labeling", Appl Environ Microbiol 2000; 66:1001-1006.

Singh, N.P., et al., "Visual quantification of DNA double-strand breaks in bacteria", Mutat Res 1999; 429:159-168.

Singh, N.P., "A Simple Method for Accurate Estimation of Apoptotic Cells", Exp Cell Res 2000; 256:328-337.

Steensma,D.P., "Flow Cytometric Methods for Detection and Quantification of Apoptosis", Methods Mol Med 2003; 85:323-332.

Tamayo, M. et al. " Rapid assessment of the effect of ciprofloxacin on chromosomal DNA from *Escherichia coli* using an in situ DNA fragmentation assay", BMC Microbiology 2009, 9:69 (11 pp).

Gorczyca, W., et al., "Detection of DNA Strand Breaks in Individual Apoptotic Cells by the in Situ Terminal Deoxynucleotidyl Transferase and Nick Translation Assays", Cancer Research 1993, 53: 1945-1951.

Fernandez, J.L., et al., "Simple determination of human sperm DNA fragmentation with an improved sperm chromatin dispersion test", Fertility and Sterility vol. 84, No. 4 (2005): 833-842.

Fernandez, J.L., et al., The Sperm Chromatin Dispersion Test: A Simple Method for the Determination of Sperm DNA Fragmentation, Journal of Andrology, vol. 24, No. 1, 2003: 59-66.

Muriel, et al., "Structure of human sperm DNA and background damage, analysed by in situ enzymatic treatment and digital image analysis", Molecular Human Reproduction, vol. 10, No. 3, 2004: pp. 203-209.

Russian Office Action dated Oct. 28, 2009, issued in corresponding RU Application No. 2009117464/10 (10 pp).

Russian Office Action dated Aug. 7, 2009, issued in corresponding RU Application No. 2009117464/20 (2 pp).

Japanese Office Action dated Apr. 12, 2012, issued in corresponding JP Application No. 2009-535757 (4 pp).

EP Office Action dated Jul. 5, 2013, issued in related EP Application No. 07823042.2 (5 pp).

EP Intent to Grant dated Mar. 20, 2014, issued in related EP Application No. 07823042.2 (48 pp).

EP International Search Report dated Mar. 3, 2008, issued in related International Application No. PCT/ES2007/000637 (4 pp).

Vasquez, M., et al., "Comparative analysis of apoptosis versus necrosis using the single cell gel (SCG) assay" Environ Mol Mutagen 1997; 29:53.

Stratagene Catalog p. 39 (1988).

Fernandez, et al., "DNA fragmentation in microorganisms assessed in situ", Applied and Environmental Microbiology, 2008, vol. 74, No. 19, pp. 5925-5933.

EP Supplementary European Search Report and Opinion dated Jan. 15, 2010, issued in corresponding EP Application No. 07823042.2 (9 pp).

Corresponding EP Patent Application No. 07823042.2; Decision to Grant dated Jul. 10, 2014, 2 total pages.

Corresponding IL Patent Application No. 198623; Notice of Allowance dated Jul. 3, 2014, 5 total pages.

Corresponding EP Patent Application No. 12817952.0; Extended European Search Report dated Mar. 11, 2015, 8 total pages.

\* cited by examiner

METHOD FOR DETERMINING DNA FRAGMENTATION IN MICROORGANISMS

This United States Patent Application is a continuation of U.S. patent application Ser. No. 12/513,560, filed May 5, 2009, now U.S. Pat. No. 8,492,086, issued Jul. 23, 2013, which is the United States National Stage of Patent Cooperation Treaty Application No. PCT/ES2007/00637, filed Nov. 11, 2008, which is a continuation of Spanish Patent Application No. P200602859, filed Nov. 10, 2006, each hereby incorporated by, reference herein.

The present invention is comprised within the field of biotechnology industry, and mainly that related to microbiology, the scope of application of which is comprised within the healthcare (human, veterinary, environmental and basic) sector.

It specifically relates to a process for determining DNA integrity in microorganisms, given that cell death means DNA fragmentation, and a kit for evaluating the DNA integrity in microorganisms.

STATE OF THE ART

Microbes can die due to different causes. In the case of bacteria, which are organisms with a special health interest, the final death mechanism due to the action of antibiotic agents is virtually unknown, most likely due to the obviousness of the problem. Antibiotics affect important cell processes, which sooner or later will lead to the death of the cell. In spite of the knowledge of the initial mechanism of action of a specific antibiotic, sometimes it is not possible to clearly distinguish a bacteriostatic or bactericide effect. This picture of cell death is especially complicated due to the recent description of the presence of a small proportion of persisting cells invulnerable to bactericide antibiotics, in spite of being mutant and not growing in the presence of the antibiotic. Said persistent cells seem to explain the high resistance of biofilms and of stationary cultures to death by chemotherapeutic agents.

In addition, transcription profile studies of all *Escherichia coli* genes have demonstrated the existence of a group of genes which are induced and others which are repressed in a common manner after the action of antibiotics, the mechanism of action being very different. This was verified with ampicillin, a cell wall synthesis inhibitor, and with ofloxacin, a fluoroquinolone blocking DNA gyrase and topoisomerase IV, inducing direct damage in DNA (Kaldalu N, Mei R, Lewis K. Killing by ampicillin and ofloxacin induces overlapping changes in *Escherichia coli* transcription profile. Antimicrob Agents Chemother 2004; 48:890-896.)

This knowledge suggests that cell death in bacteria, after the action of a bactericide antibiotic for example, could be a programmed process, like the apoptosis phenomenon present in higher organisms. A similar phenomenon has been described in single cell yeasts as a response to the action of fungicide agents. The autolysis of bacterial cells by self-digestion of the cell wall by autolysins after exposure to antibiotics or adverse environmental conditions can be an expression of the programmed cell death of defective organisms (Lewis K. Programmed Death in Bacteria. Microbial Mol Biol Rev 2000; 64: 503-514.)

Since the start of microbiology, most chemotherapeutic action studies have been routinely evaluated, assessing cell growth as the capacity to produce colonies in a semisolid culture medium or to cause turbidity in a liquid medium. In addition to being relatively long, this system does not evaluate the behavior of each cell but rather the group in general, and is only applicable to the microorganisms with the capacity to be cultured in vitro. To study the life stage of each cell, it is necessary to use microscopy or cytometry techniques. (Lecoeur H. Nuclear apoptosis detection by flow cytometry: influence of endogenous nucleases. Exp Cell Res 2002; 277: 1-14; Steensma D P, Timm M, Witzig T E. Flow cytometric methods for detection and quantification of apoptosis. Methods Mol Med 2003; 85:323-332).

A possible, although not usual, evaluation is to assess the permeability of the cell wall and of the cell membrane using vital dyes. The cell is only stained with the vital dye if it has an alteration of the barrier isolating it from the exterior, which is usually linked to lysis by osmotic shock. Whether it is by direct damage, through enzymatic systems or through the loss of membrane integrity, the DNA of the chromosome of the microorganism must be fragmented in the cell death process. However, chromosomal DNA integrity has not been evaluated as a microbial death parameter in in situ cell-by-cell studies. This is due to the absence of a feasible, reliable and reproducible technique for determining chromosomal DNA integrity with a small size in relation to that of cells of higher organisms.

There are different well-established in situ methodologies for evaluating the DNA integrity of cells of higher organisms in relation to the induced damage and to cell death by apoptosis or necrosis. The labeling of DNA breakages in situ by introducing labeled nucleotides therein using enzymes such as terminal transferase (TUNEL) or the DNA polymerase (in situ nick translation ISNT) are emphasized among such methodologies (Didenko V, ad. In situ detection of DNA damage. Humana Press, Totowa, N.J., 2002.)

These methodologies are based on the use of enzymes on cells fixed in slides, which enzymes act on 3'-OH ends of the breakages, i.e. without chemical modifications. For said reason, their efficacy is irregular, only those breakages accessible for the enzyme being labeled, which means a relatively low reproducibility of the results. There is only one work in which the TUNEL technique for detecting bacterial DNA breakages in *Escherichia coli* and the archaeon *Haloferax volcanii* is applied (Rohwer F and Azam F. Detection of DNA Damage in Prokaryotes by Terminal Deoxyribonucleotide Transferase-Mediated dUTP Nick End Labeling. Appl Environ Microbiol 2000; 66:1001-1006.)

This study demonstrated the capacity to detect bacterial DNA fragmentation after infection by a phage. However, the breakages caused directly by hydrogen peroxide in certain conditions were not detected. This can be due to the impossibility for the enzyme to label breakages with modified 3'-OH ends, which is a problem of this technique. In addition, the cells must be fixed in order to perform these techniques, which affects the labeling capacity. Furthermore, the reagents are expensive, therefore these techniques are only applied in research studies, it not being possible to use them for the routine assessment of DNA damage and deterioration. These techniques are relatively long and complex, therefore they are not normally used in microbiology and no other work in relation thereto has been described.

Another microscopy technique for the in situ cell-by-cell study of the DNA integrity is the comet assay or single-cell electrophoresis (Olive P L, Durand R E. Heterogeneity in DNA damage using the comet assay. Cytometry 2005; 66:143.)

Eukaryotic cells are included in an agarose microgel on a slide and are subjected to lysing solutions to extract the membranes and the proteins. Nucleoids, i.e. deproteinized nuclei are thus obtained in which the DNA loops have relaxed due to decompaction. The nucleoids are subjected to electrophoresis in a tank filled with buffer solution, such that the DNA fibers migrate towards the anode, forming a comet image with a head and a tail in the direction of electrophoretic migration. These comets are stained with a fluorescent dye in order to be observed by means of fluorescence microscopy. If the nucleus has DNA fragmentation, a large amount of fragments thereof will have migrated, being concentrated in the tail of the comet. It is a quite sensitive but relatively expensive and complicated test for a conventional clinical laboratory. In fact, it requires certain uncommon instruments: electrophoresis power supply and tank and a system for capturing and analyzing images. Due to the foregoing, it is only used for research purposes. There is only one published work in which the comet technique is applied at a neutral pH in the *Escherichia coli* bacterium (Singh N P, Stephens R E, Singh H, Lai H. Visual quantification of DNA double-strand breaks in bacteria, Mutat Res 1999; 429:159-168.)

The technique is long and complicated, requiring multiple incubations and the interpretation of the images in relation to the DNA breakages is not clear. Therefore, no other work with this technique in bacteria has been described.

From that described above it is deduced that there is still a need for a reliable process which can be used routinely and simply for the in situ study of chromatin/DNA integrity in microorganisms. A methodology must be developed or adapted that is much quicker and more effective for evaluating bacterial death, placing special emphasis on the death which is generated by or translates into DNA degradation. This is thus a field in which hardly any innovations have been provided. The process must be robust, easy to implement, cheap and accessible for a basic laboratory. It must furthermore give homogeneous results between different laboratories and must be able to be automated. The DNA diffusion assay is somewhat similar to the single cell electrophoresis assay, allowing the evaluation of the fragmentation thereof. The cells immersed in an inert agarose gel, on a slide, are subjected to lysis. If the cells have fragmented DNA, the fragments diffuse in the agarose matrix from the initial nucleus, wide halos of peripheral DNA fragment diffusion being observed (Vasquez M, Tice R R, Comparative analysis of apoptosis versus necrosis using the single cell gel (SCG) assay. Environ Mol Mutagen 1997; 29:53.). This has been applied to eukaryotic cells, mainly of a somatic type. The cells showing DNA fragment diffusion correspond to those which have died due to an apoptotic process (Singh N P. A simple method for accurate estimation of apoptotic cells. Exp Cell Res 2000; 256:328-337.).

Some variants of this assay have been successfully applied to human sperm cells and sperm cells of other animal species by this research group, and are called Sperm Chromatin Dispersion (SCD test), (Rodriguez S, Goyanes V, Segrelles E, Blasco M, Gosálvez J, Fernández J L. Critically short telomeres are associated with sperm DNA fragmentation. Fertil Steril 2005; 84: 843-845.; Enciso M, López-Fernández C, Fernández J L, García P, Gosálbez A, Gosálvez J. A new method to analyze boar sperm DNA fragmentation under bright-field or fluorescence microscopy. Theriogenology 2006; 65:308-316.).

The main differences of the variant of the process of the present invention in relation to the technique described for sperm cells are the following:

The first incubation with an acid solution is not necessary, only lysis being necessary.

The solution for lysing sperm cells is not active in microorganisms like bacteria. Triton X-100 is not active for lysing these microorganisms. To that end, it is recommendable for the lysis to contain a stronger detergent with the capacity to denature proteins, such as SDS, and adding EDTA as a chelating agent aiding to destabilize the cell walls.

Technically these differences mean the lysis of the bacterial wall, conserving the DNA integrity. The latter point is important because since bacterial DNA is relatively lacking in proteins in relation to that of eukaryotic cells, it could be more susceptible to iatrogenic damage generated during handling and processing.

The use of highly sensitive fluorescent dyes, such as those of the SYBR family, SYBR Gold for example, allows discriminating the DNA fiber of the nucleoids of the microorganism and especially accurately viewing the small DNA fragments diffused in the agarose in the event of fragmentation of such DNA. This is not possible using classic DNA fluorochromes such as propidium iodide (PI), ethidium bromide, acridine orange Hoechst 33258 or 33342, or DAPI.

Another additional advantage is that the necessary incubation time in lysis is much shorter, resulting in a much quicker methodology compared to that described in sperm cells.

In the present invention, it is essential to stabilize the DNA nucleoid of the microorganism in order to be viewed with the fluorescence microscope. This small nucleoid is very delicate, being detached and progressively and quickly degraded into the liquid staining medium upon being exposed to the light of the fluorescence microscope. This is an essential technical problem that does not occur with the nucleoids of sperm cells or other cell types of higher organisms with a much greater mass. In the case of microorganisms, to stabilize the nucleoid and adhere it firmly to the slide, a dry intense heat incubation step is carried out. Thus, once the slide with the nucleoids has dried, before the staining, it is incubated in a microwave oven at high power (750-1000 W) for 10 minutes. It can subsequently be stained and viewed. Another possibility is to incubate the slide in an oven at high temperature, 80-100° C., for hours. However, the use of the microwave oven speeds up the process enormously, aiding in carrying out the technical protocol quickly. This stabilization step is essential in the invention so that the process has a high added value in the preparation of a commercial end product.

It can be deduced from the foregoing that the process of the present invention results in microorganism nucleoid images, being able to clearly discriminate those containing fragmented DNA. Consequently, with said process, the determination of the DNA fragmentation levels of the sample is simple and reliable, which enables it to be used routinely and at a low cost. Its application is relevant in different clinical and basic microbiological laboratories with samples of microorganisms.

However, an assay with these characteristics has never been applied to determine the DNA integrity of microorganisms. The adaptation and adjustment of this methodology for evaluating genomes with a relatively small size, after previously achieving the lysis of the bacterial walls in order to allow DNA diffusion in the event of fragmentation of such DNA would have an enormous potential interest. A relatively simple and quick tool would then be available which would allow assessing in situ, cell by cell, the presence of DNA breakages in bacteria and other microorganisms in a reproducible manner. The viewing at a microscopic level of a fragmented DNA molecule after the action of lytic agents can be used to quickly analyze bacterial cell death. The interesting and multiple potential applications of said methodology in research, hospital, veterinary or environmental protection applications are detailed below:

Monitoring of agents with potential capacity to directly or indirectly damage and fragment DNA, which are physical (ionizing radiations, ultraviolet radiations), chemical (antiseptic, antibiotic, chemotherapeutic and antimicrobial agents in general), biological and enzymatic (repair enzymes, restriction enzymes encoded by additional modules or phages).

Monitoring of susceptibility to both known and new antimicrobial drugs.

Determination of the effectiveness of agents with the capacity to damage and fragment DNA depending on different experimental or environmental conditions.

Monitoring of the stress at DNA level in natural microorganism populations or in different laboratory conditions (nutrients, aging, variations of physicochemical agents such as temperature, pH, osmotic pressure, light, etc.).

Analysis of the sensitivity to damage induction of the DNA of different wild and mutant lines, for example strains resistant to antimicrobial agents, as well as its repair.

DESCRIPTION OF THE INVENTION

The object of the present invention relates to a process for evaluating the DNA integrity of microorganisms simply, quickly and accurately, and which can be incorporated into the routine activity of any microbiological research laboratory.

Thus, a first object of the invention consists of a process for evaluating the DNA integrity of a microorganism, comprising the following steps:

a) immobilizing the microorganism on a slide, without fixing, by means of including it in an inert medium;

b) treating with a lysis solution to extract cell walls, membranes and proteins, retaining the DNA of the microorganism;

c) stabilizing the DNA nucleoid of the microorganism on the slide; and d) staining and evaluating the DNA integrity.

The microorganisms are initially included in a medium similar to an aqueous suspension, preferably in an inert microgel, especially in an agarose microgel, which can be prepared on a suitable support, for example on a glass cover slip.

The selection of the lysis solution is critical for reaching the objectives of the present invention. It is essential to use anionic or cationic protein denaturing detergents, such as sodium dodecyl sulfate (SDS), alkylbenzene sulfonate, N-lauryl sarcosine (sarkosyl), hydrated salt of glycolic acid, and mixtures thereof, preferably using SDS. They are detergents causing a high membrane disruption with lysis effects and at the same time they are active protein denaturing agents. They are used in denaturing electrophoresis in which the proteins are subjected to migration, ensuring the complete denaturation (loss of the three-dimensional structure). Their activity within detergents is high. The use of a non-ionic non-protein denaturing detergent, i.e. a detergent solubilizing the proteins but not denaturing them, is usually not efficient to lyse effectively in many microorganisms. The inclusion of ethylenediaminetetraacetic acid (EDTA) is important since it acts as an Mg++ cation chelating agent, which cations stabilize the outer membrane of bacteria, especially in the coat of Gram-negative bacteria. It is also possible to include lytic proteins, both of the cell wall and of proteins.

It is preferred that the lysis solution contains other agents favoring the destabilization of cell walls and subsequent extraction. It has been verified that an effective solution is that containing between 0.001 and 2M dithiothreitol (OTT), 0.001 and 2M 2-amino-2-(hydroxymethyl)-1,3-propanediol (Tris), between 0.001 and 2M EDTA, and between 0.1 and 3% SDS, at a pH between 6.5 and 10.5. A solution containing about 0.1M OTT, about 0.01M Tris, about 0.05M EDTA and about 2% SDS, at a pH of about 10 is particularly suitable.

After the lysis, the DNA nucleoids must be stabilized in the slide so that they do not degrade and become detached upon being exposed to the light of the fluorescence microscope. The quickest and most effective system is to incubate the slide, after having been dehydrated, incubating in increasing alcohol baths and drying in a microwave oven. The heat generated firmly adheres the nucleotide to the slide. This is an essential, specific step of the present invention. Different powers can be assayed for different times. One possibility is to use maximum power for 2-15 minutes. Another possibility, which is less recommendable because it lengthens the duration of the technique, is to incubate the dry slide in an oven or drying oven at a high temperature, 40-100° C., for one or several hours.

The process according to the present invention has a step of evaluating DNA integrity of microorganisms, after steps a), b) and c). Although there are several alternatives for this evaluation, it is preferred that it be visual. For this purpose, the process preferably includes a step of staining the sample after steps a), b) and c). Given the relatively small size of the DNA of microorganisms, said staining must be carried out with a highly sensitive dye using a microscope with a high magnification lens (normally 100x). Therefore, systems based on fluorescence microscopy using DNA-specific fluorochromes, and specifically those providing the best sensitivity and stability, are preferable. The list is extensive and grows continuously. GelRed, EvaGreen, and other cyanine derivatives such as the SYBR families, those of PicoGreen, the variants of TOTO, YOYO, BOBO, POPO, JOJO, LOLO, SYTOX, PO-PRO, BO-PRO, YO-PRO, TO-PRO, JO-PRO, PO-PRO, LO-PRO, etc, can be mentioned as examples.

The evaluation of the results can be carried out by the observer, assigning each nucleoid observed to a previously established damage scale. It can also be preferably assessed using a system for capturing digitized images, coupled to software quantitatively determining the damage level.

A second object of the present invention consists of the manufacture of a kit for evaluating DNA integrity of microorganisms, essentially comprising:

a) pretreated glass slides for supporting and retaining the microgel with the microorganisms;

b) a solution for mixing and including the microorganisms in microgels;

c) a lysis solution for extracting walls, membranes and proteins; and d) a fluorochrome for staining the DNA.

The kit allows carrying out the previously described process.

A third object of the present invention relates to the development of software for the automated measurement of the DNA fragmentation levels of the microorganism.

Figure 1:
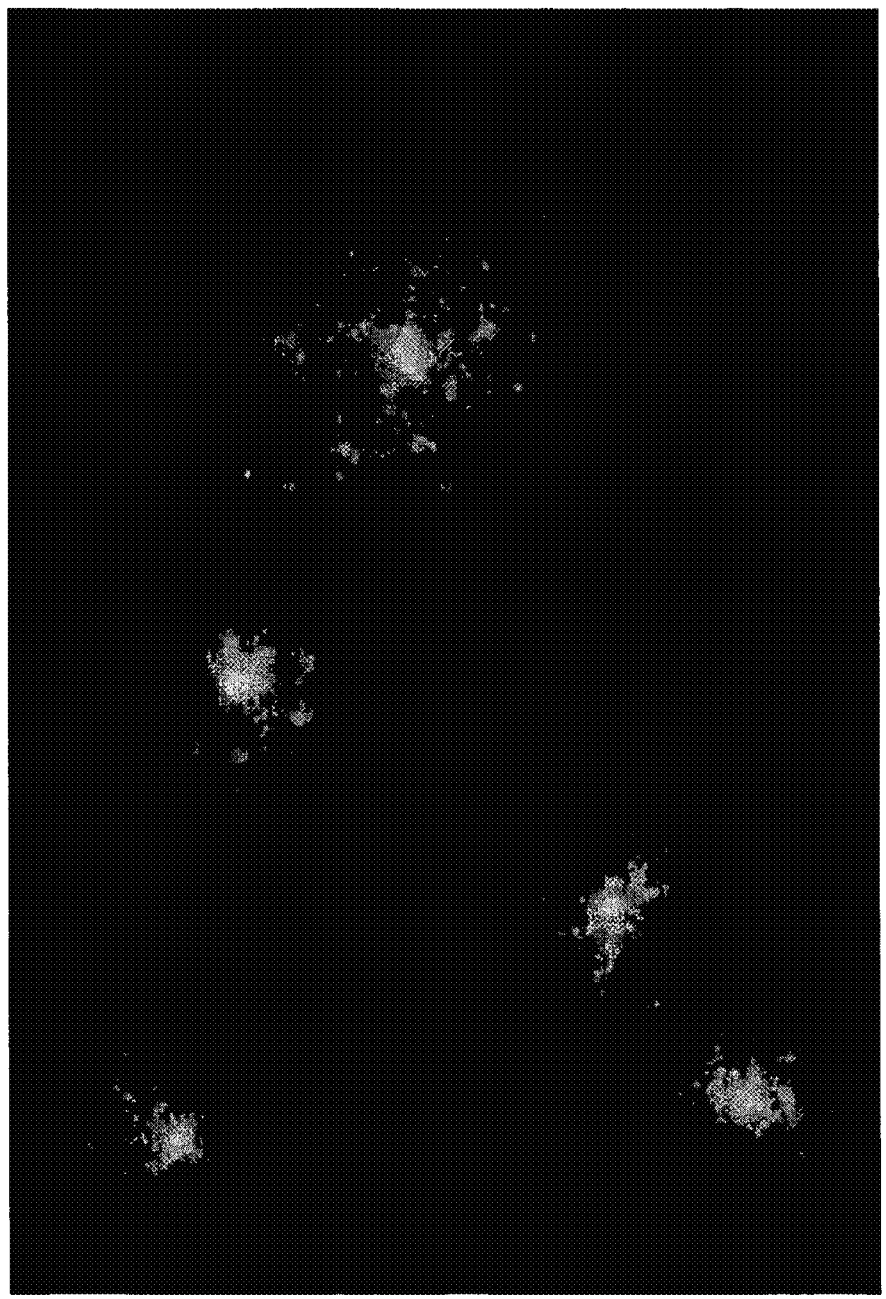
FIG. 1 shows nucleoids from an *Escherichia coli* cell culture, obtained after applying the process described in the invention. The intact nucleoids are compact, flattened on the slide, continuity solutions suggesting DNA fragmentation not being observed. A nucleoid with the massively fragmented DNA (above) from a spontaneously dead cell is occasionally observed in the culture.

a: intact nucleoid (level 0).

b: Nucleoid with discrete peripheral fragments with a relatively large size, after DNA breakages (level 1, low damage).

c: More relaxed nucleoid, occupying a larger surface, with discrete peripheral fragments with a relatively large size, after DNA breakages (level 2, medium damage).

d: Much more relaxed and extended nucleoid, with a larger number of peripheral fragments, after DNA breakages (level 3, high damage).

e: Nucleoid with massive DNA fragmentation, formed by multiple small fragments which diffused in the agarose matrix, after lysis, delimiting a wider diffusion surface (level 4, massive damage).

Figure 3:
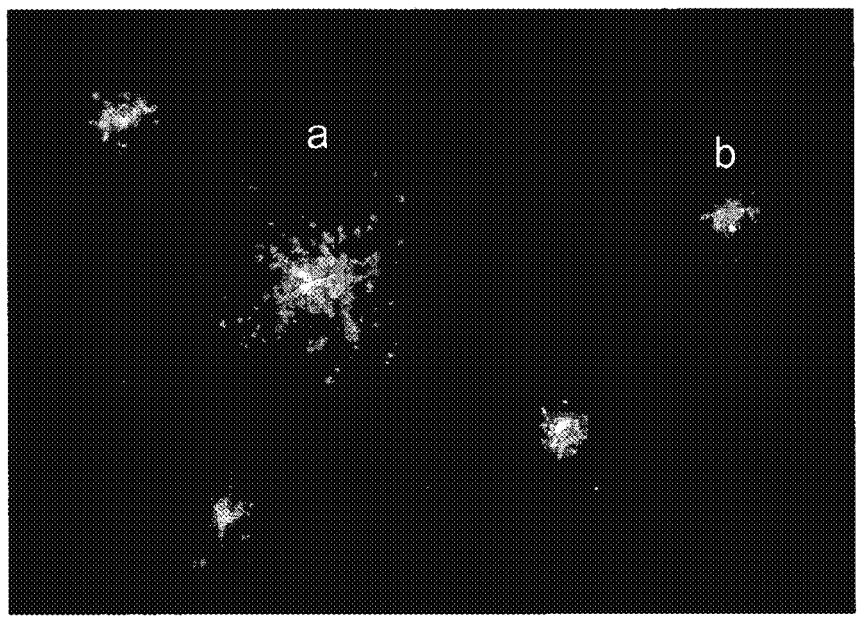

FIG. 3 shows the DBD-FISH technique for detecting DNA breakages, hybridizing a total genomic *Escherichia coli* DNA probe labeled with Cy3 (A). The nucleoid with fragment diffusion has an intense labeling thereof, whereas the remaining nucleoids only show a very discrete baseline labeling. The DNA was counterstained with DAPI (B).

Figure 4:
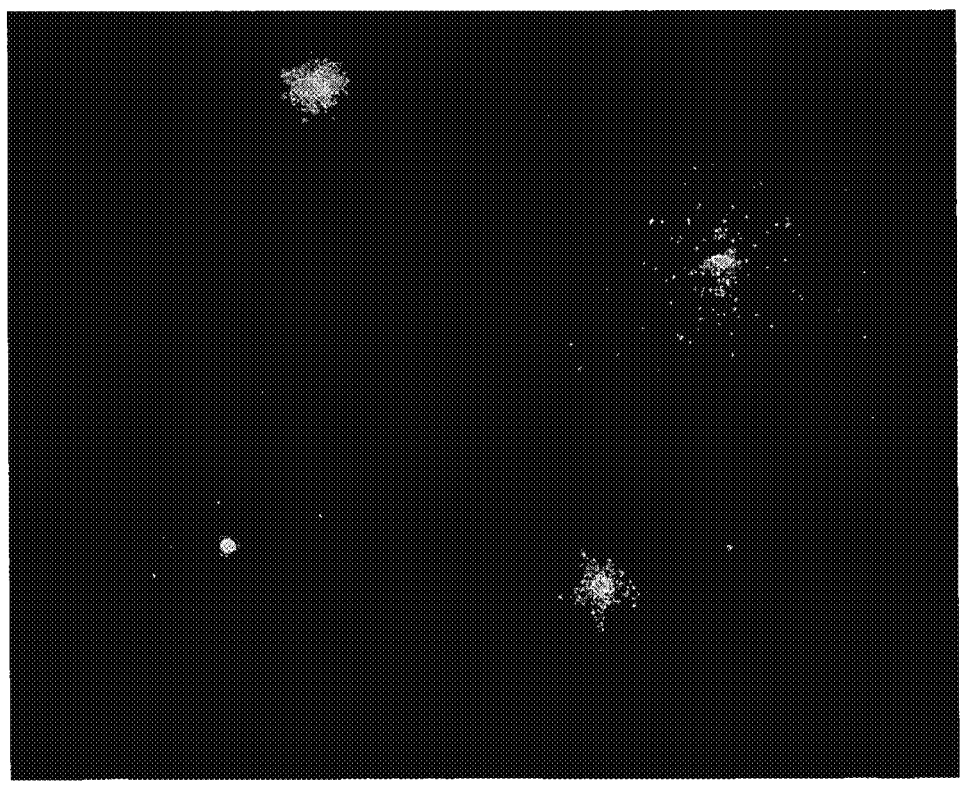

FIG. 4 shows the application of the method of the invention to an *Acinetobacter baumannii* sample. Two intact nucleoids and another two nucleoids with DNA crushed into fragments are shown.

Figure 5:
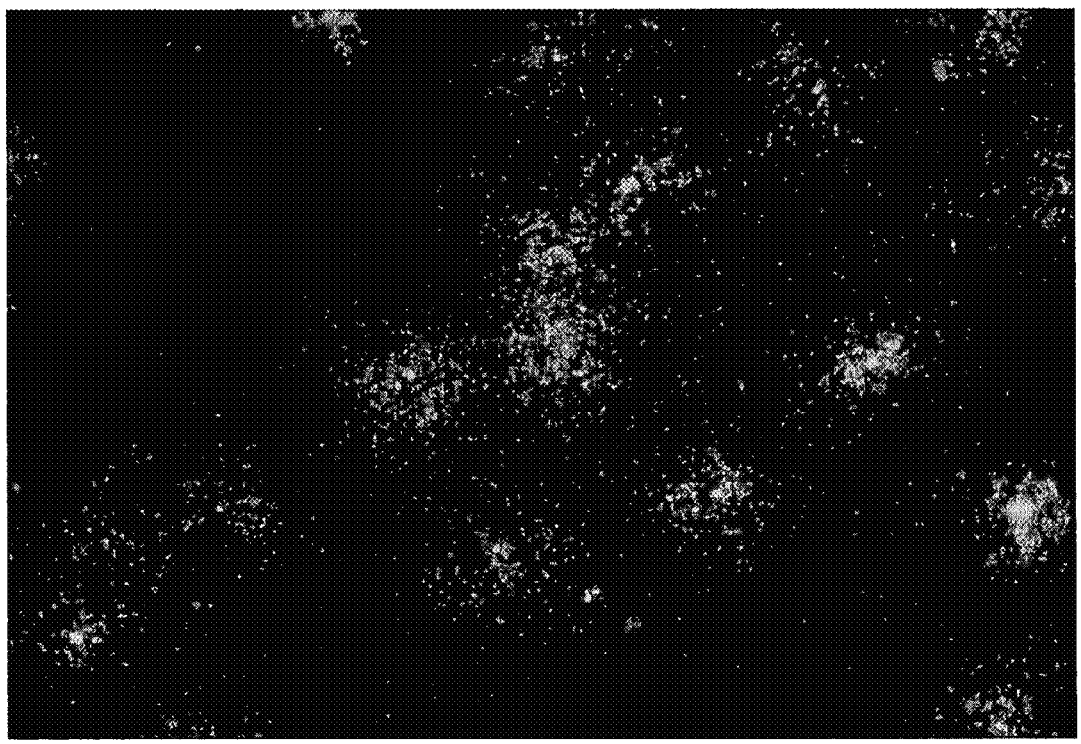

FIG. 5 shows massive *Escherichia coli* DNA fragmentation after exposing the bacteria to 10 mM hydrogen peroxide for 10 minutes.

Figure 6:
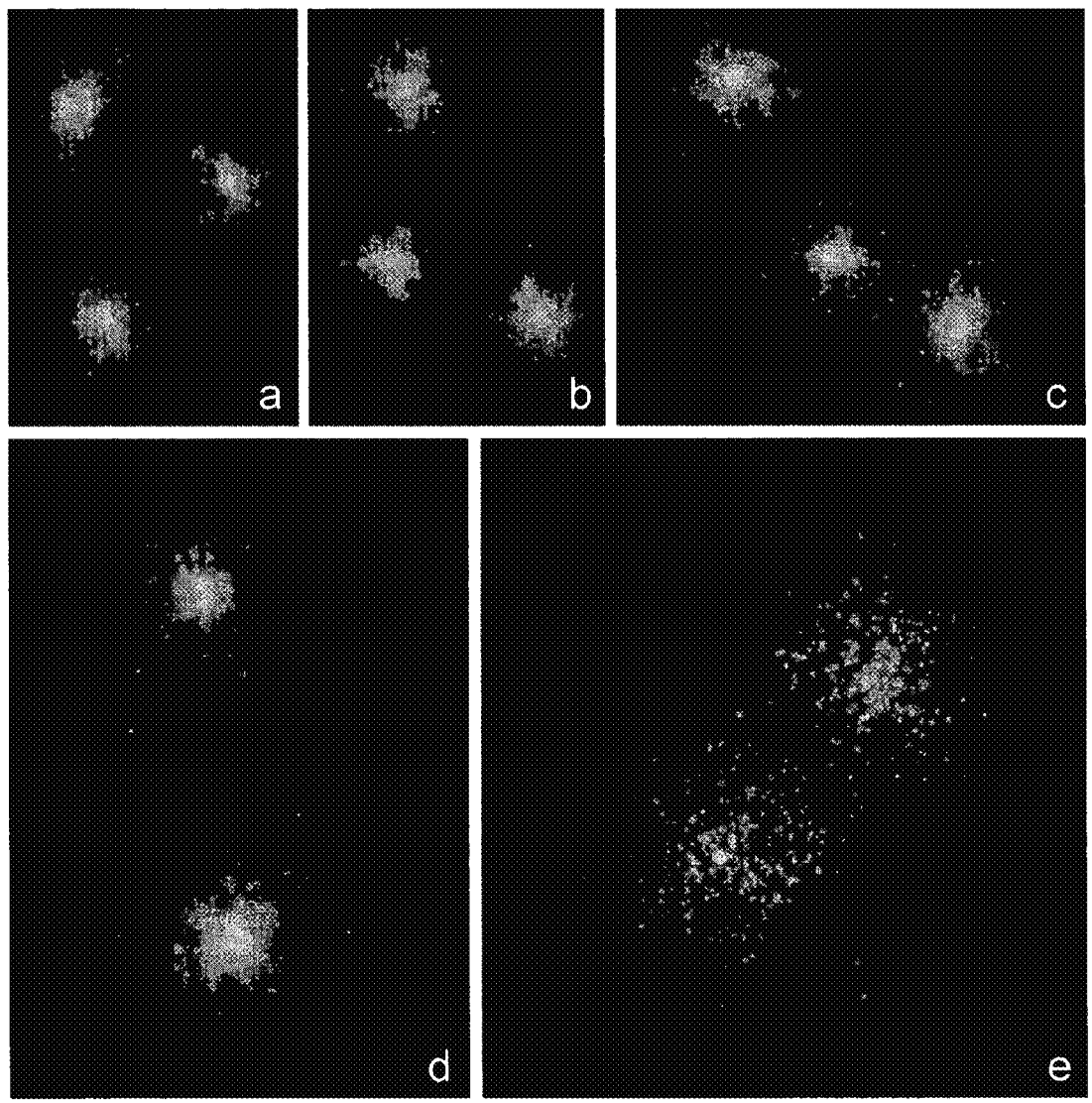

FIG. 6 shows the *Escherichia coli* DNA damage, observed after different incubation times with ciprofloxacin (1 µg/ml), a: 0 minutes. b: 2.5 minutes. c: 5 minutes. d: 15 minutes. e: 40 minutes. An initial damage level is already observed after 5 minutes, increasing progressively with longer incubation times.

Figure 7:
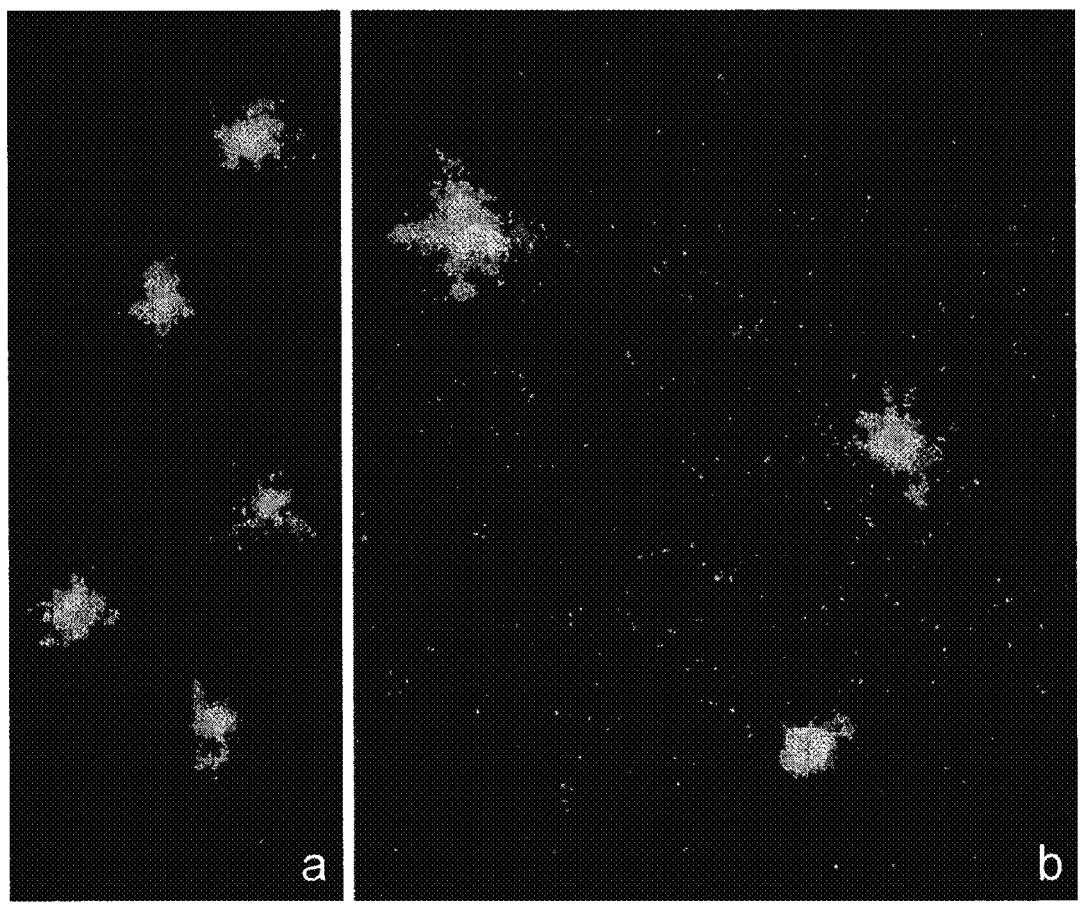

FIG. 7. *Escherichia coli* nucleoids observed after incubation with ampicillin (300 µg/ml) for 20 minutes (a) and after 24 hours (b). DNA fragments are not observed after 20 minutes, whereas after 24 hours, the bottom is covered with DNA fragments.

Figure 8:
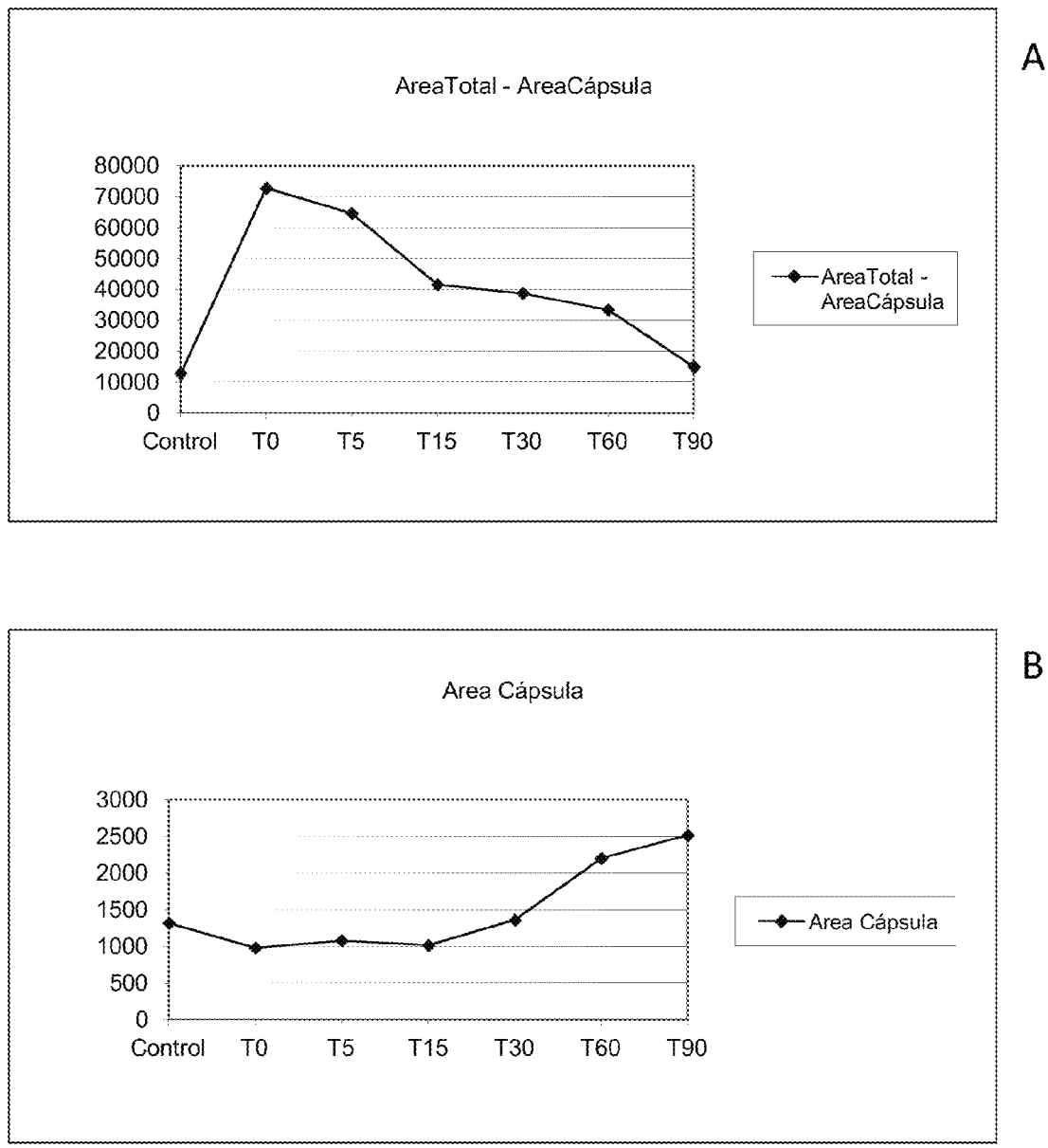

FIG. 8 shows graphs depicting the area average evolution (in pixels, y-axis) of the fragment diffusion halo or loop relaxation of the *Escherichia coli* nucleoid (A), and of the capsule (B), in relation to the time after incubation with 10 micrograms/ml of ciprofloxacin, 40 minutes (x-axis).

Figure 9:
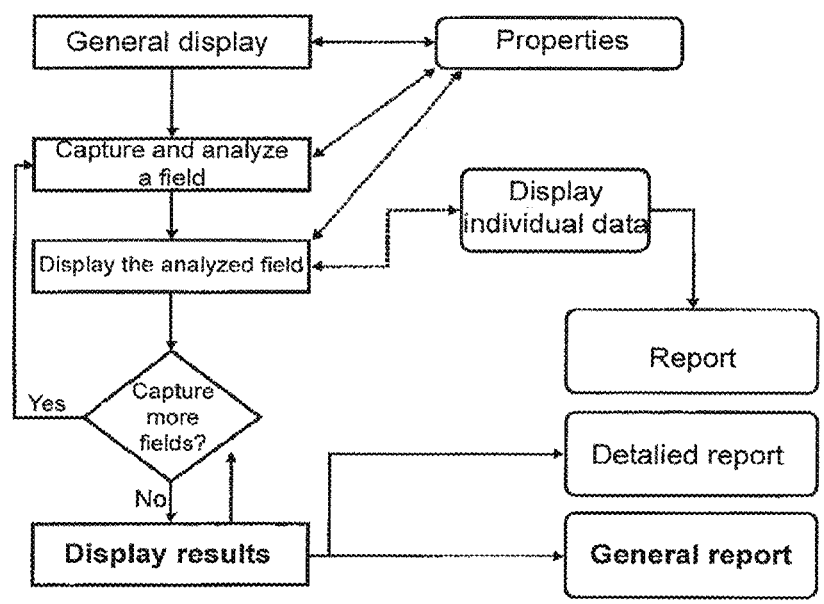

FIG. 9 shows the diagram of the routine to be followed for the step-by-step measurement and with decision-making process for bacterial DNA fragmentation with the generation of a final report.

Figure 10:
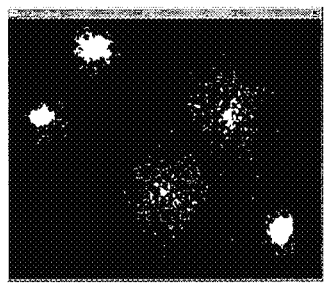
Figure 10:
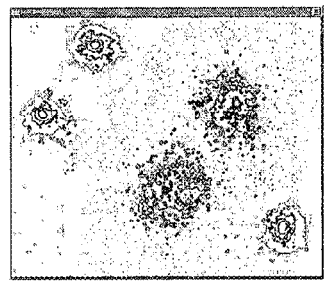
Figure 10:
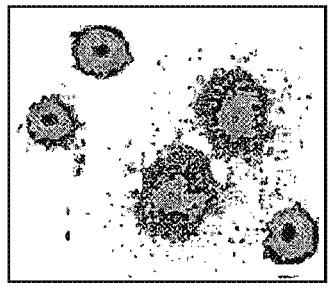
Figure 10:
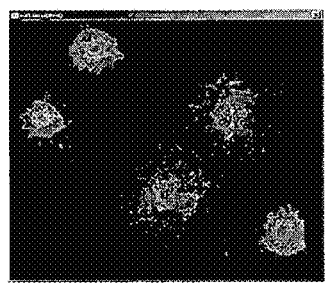

FIG. 10 shows a sample of three processes for segmenting and delimiting the ROIs carried out on a digital capture showing a bacterial field including 3 bacteria with normal DNA and 2 bacteria with fragmented DNA (upper left image). The remaining images correspond to electronic filters of the original image which can be useful as a strategy to be followed in order to distinguish both cell types more easily.

Figure 11:
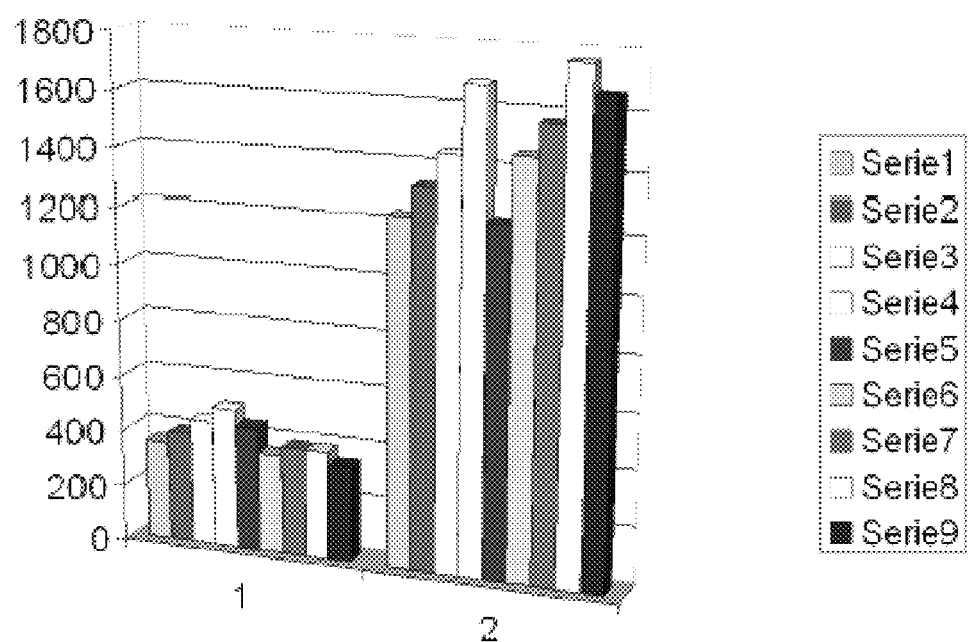
Figure 11:
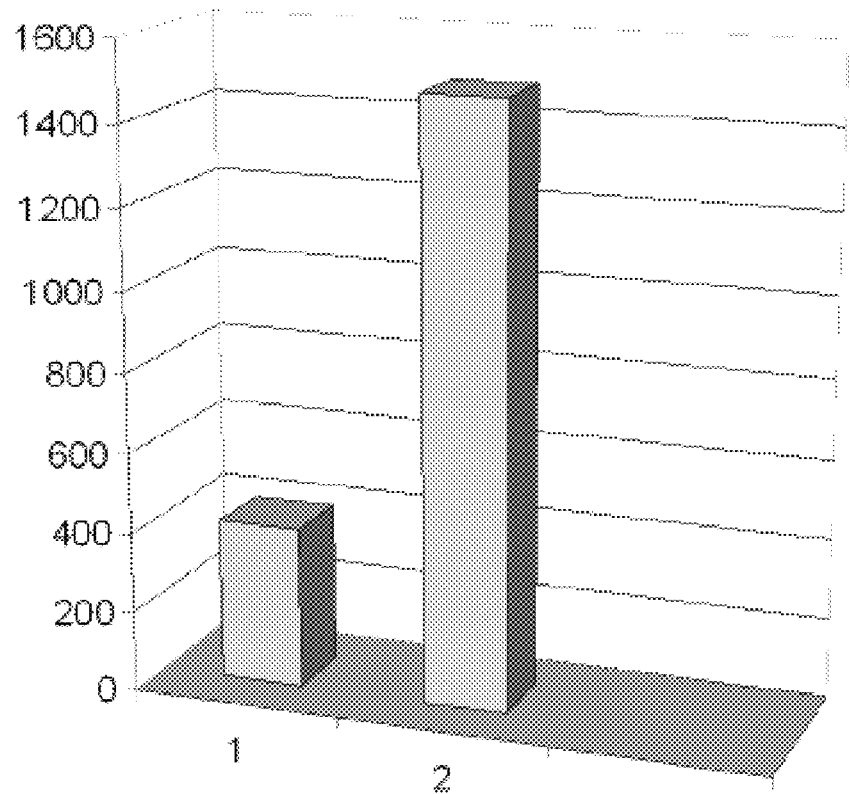

FIG. 11 shows the average integrated density in 9 different experimental series in which bacteria with non-fragmented DNA (1) and bacteria with fragmented DNA (2) were chosen. The upper part of the figure shows the averages per experiment, whereas the lower part shows the overall average per group according to the non-fragmented DNA (1) versus fragmented DNA (2) criterion.

DETAILED DESCRIPTION OF THE INVENTION

As will be detailed below, the process and kit of the present invention are a simple and reliable system for determining the frequency of microorganisms with fragmented DNA.

The process of the invention, which allows evaluating the DNA integrity of a microorganism, comprises the steps of:

a) immobilizing the microorganism on a slide, without fixing, by means of including it in an inert medium;

b) treating with a lysis solution to extract cell walls, membranes and proteins;

c) stabilizing the nucleoid DNA on the slide; and d) staining and evaluating the DNA integrity.

The process of the invention, together with some variants and optional steps, is detailed below. The person skilled in the art will understand that there are other embodiments and possibilities provided that the described essential aspects are maintained.

A) The first step is the preparation of the sample. By means of usual processes in the field the concentration of microorganisms in a liquid sample is obtained and verified. The suitable concentration for the analysis ranges between 0.1 and 20 million microorganisms per milliliter. If the sample were excessively concentrated, it is adjusted to the suitable concentration by diluting it with culture medium or with saline/phosphate buffered solution (PBS) or the like, suitable according to the microorganism.

It is recommendable to carry out the processing in low luminosity conditions to prevent photoinduced DNA damage during handling and incubations. The sample must be placed on a support for its processing according to the process of the invention and to facilitate its evaluation. The support is preferably as glass slide which is coated with a standard agarose film. To that end, a standard agarose solution between 0.2 and 1% in distilled water is prepared in a Coplin jar or the like. It is covered with a perforated plastic sheet and deposited in a microwave oven. The microwave oven is adjusted to a power between 300-1000 W, preferably to 500 W, stirring the container occasionally for a better agarose dissolution. This process can also be carried out using a thermostatic bath. When the age rose solution becomes completely transparent, it will be ready to be deposited in vertical vessels with a content between 10 and 250 ml. These vessels must be previously attempered in a bath between 50-100° C., preferably at 70° C., to maintain the agarose solution in liquid state.

The slides must be clean. They are submersed vertically, holding them with tweezers by the ground area between 1-60 seconds, removing them and submersing them again between one and ten times, until forming a homogeneous film on the slide. They are deposited horizontally on a smooth and cold surface between 1 and 15° C., preferably at 4° C., made of glass or metal for example. This plate with the slides is introduced in the refrigerator at 4° C. for at least 30 minutes, until verifying that the agarose solution has gelled on the surface of the slide. The trays are removed from the refrigerator and the surface of the slides which was in contact with the plate is cleaned with blotting paper. The slides are then introduced horizontally in a drying oven at a temperature range of 37-100° C., until the agarose has dried completely and forms a fine film adhered to the glass. The slides thus treated can be used immediately or stored in a well closed box at room temperature for several months.

To facilitate the processing of the sample containing the microorganisms, it is introduced in a medium with features similar to those of a suspension, such as an agarose microgel for example. In this case, a low melting/low gelling point agarose solution is prepared at a concentration comprised between 0.5 and 2% in distilled water or phosphate buffered saline (PBS). This agarose is melted using a microwave oven or a thermostatted bath, and is subsequently maintained between 30 and 37'C in a tube introduced in a thermostatted bath or drying oven. In an Eppendorf tube or the like, the sample and the agarose solution are carefully mixed, such that the latter is at a concentration between 0.3 and 1%; for example, 70 microliters of the agarose solution+30 microliters of the sample. It is important for the temperature of the agarose to not be greater than 37° C., in order to not damage the microorganisms.

Finally, to obtain the sample on the support, the coated slides are placed on a smooth and cold glass or metal surface, with a temperature ranging between 1 and 15° C., preventing the formation of air bubbles. The deposition with a micropipette of a drop between 5-200 microliters of the mixture is recommended, placing a cover slip on top of the drop. As a precaution, the processing of each sample in duplicate and the use of a control sample every time the technique is applied is recommended. The plate with the slides is introduced in a refrigerator at 4'C, between 2 to 30 minutes until a suitable gelling of the agarose occurs. Once the gelling has occurred, the cover slips are gently removed inside the refrigerator, preventing the damage of the microgel.

B) Once the samples have been suitably prepared for their easy and repeated handling, they are treated according to the process of the invention with a lysis treatment step to extract walls, membranes and proteins. To that end, each slide is submersed in a horizontal position in a vessel containing the lysing solution.

In a preferred embodiment, this solution is formed by: between 0.001 and 2M, preferably between 0.01 and 0.8M, dithiothreitol (DTT); between 0.001 and 2M, preferably between 0.005-0.4M, 2-amino-2(hydroxymethyl)-1,3-propanediol (Tris); between 0.001 and 2M, preferably between 0.01-1M, ethylenediaminetetraacetic acid (EDTA), and between 0.1 and 3%, preferably between 0.5-2.5%, sodium dodecyl sulfate (SDS). This solution is adjusted to a pH between 6.5 and 10.5, preferably 10, adjusted with NaOH, for example.

There are other alternative lysis solutions, with other extra additives, or the concentrations and incubation times and temperatures of the described solution can be varied provided that its essential functional features are maintained. Thus, as alternatives to DTT, there are compounds such as beta-mercaptoethanol and other reducing agents. As alternatives to Tris, other buffer solutions such as Hepes, Mops, Pipes can be used. As an alternative to EDTA, other chelating agents such as EGTA, etc can be used. As an alternative to SDS, other cationic or anionic detergents can be used, as has been previously mentioned.

According to the solution used and the type of sample, the preparations are incubated in the lysis solution between 1 and 120 minutes, preferably between 1 and 35 minutes, a time of about 5 minutes is especially preferred; and at a temperature between 1 and 45° C., preferably 18° C.-40° C., a temperature of 37° C. is especially preferred.

After the treatment with lysis solution, the preparations can be washed to eliminate the residues of these solutions. To that end, the slides are introduced horizontally in a washing solution that is as mild as possible, avoiding chelating agents or detergents. For example, they are submersed in a horizontal position in a vessel containing abundant distilled water or a buffer solution or physiological saline for a time between 1 and 60 minutes.

The sample is then dehydrated. To that end, increasing alcohol concentrations can be used. For example, the slides are lifted and submersed in a horizontal position, in vessels with increasing ethanol concentration series, between 5 and 100%, for 30 seconds to 60 minutes each and the preparations are then allowed to air dry. The temperature of the alcohols can range from −20° C. to room temperature. It can be preferable to use alcohols at −20° C. to improve DNA precipitation, for 5 minutes each. As alternatives to the incubations in ethanol series, the preparations can be dehydrated incubating in solutions of different alcohols such as methanol, or allowing to air dry or dry in a drying oven. It is important that the slide is completely dry so that the DNA adheres thereto, since it normally becomes detached upon being exposed to the impinging light beam of the fluorescence microscope. To that end, it is recommendable to allow it to dry at a high temperature for a long time. It is recommendable, for example, to incubate it at 80° C. for at least 60 minutes.

Once they are completely dry, the already processed slides containing the sample can be stored in tiling boxes at room temperature, in the dark, for months. This facilitates the separation of the treatment process according to the invention and the subsequent step of evaluating the DNA integrity of the microorganisms. The filing allows a repeated evaluation at different intervals of several samples of one and the same microorganism.

C) After the drying, it is crucial to stabilize and firmly adhere the DNA nucleoid to the slide, since it normally becomes detached upon being exposed to the impinging light beam of the fluorescence microscope. To that end, the dry slides are incubated in a microwave oven at a power between 300-1000 W, preferably at 500 W, for 5-10 minutes. An alternative, although less recommendable due to its duration, is to incubate the slides in an oven or a drying oven at a high temperature for one or several hours. Once they are completely dry, the already processed slides containing the sample can be stored in filing boxes at room temperature, in the dark, for months. This facilitates the treatment process according to the invention and the subsequent step of evaluating the DNA integrity of the microorganisms. The filing allows a repeated evaluation at different intervals of several samples of one and the same microorganism.

D) Once the samples have been treated according to the described process, the step of staining and evaluating is carried out. There are several possible processes for evaluating the DNA integrity of the microorganisms as has been previously indicated.

In a preferred embodiment, the sample is stained, facilitating the visual evaluation. By conveniently choosing the staining conditions, a high quality of the images and a high consistency of the evaluation results can be obtained. Given the relatively small size of the genome of the microorganisms, fluorescence microscopy is chosen for viewing DNA given its higher sensitivity.

Staining for Observation Under a Fluorescence Microscope:

Depending on the availability of fluorescence filters, the samples can be stained with DNA-specific fluorochromes of the DAPI, Hoechst 33255, ethidium bromide, propidium iodide type etc. However, fluorochromes with higher sensitivity such as GelRed, EvaGreen, and other cyanine derivatives such as the SYBR families, those of PicoGreen, the variants of TOTO, YOYO, BOBO, POPO, JOJO, LOLO, SYTOX, PO-PRO, BO-PRO, YO-PRO, TO-PRO, JO-PRO, PO-PRO, LO-PRO, etc. are preferred. The amount and quality of fluorochromes is currently increasing. To prevent the loss of fluorescence, an antifading medium (for example Vectashield-Vector H-1000, DABCO; etc.) can be included. However, these media usually cause diffuse fluorescence and a clear background making the contrast of the image difficult. It is preferable to use a highly sensitive and relatively photostable fluorochrome, mounted in an aqueous buffered solution, and to evaluate the sample relatively quickly, before it dries. If necessary, the slide can be washed and stained again.

Finally, the DNA integrity of the microorganisms is evaluated.

The images obtained can be studied by means of direct visual analysis or, preferably, by applying software for analyzing digitized images obtained by means of analog or digital cameras coupled to microscopy platforms (Example 9).

The study of at least 500-1000 microorganisms per sample is initially recommended, adopting the following DNA damage scale (FIG. 2):

1. Level 0: Microorganisms without fragmented DNA: the DNA nucleoid is maintained relatively compact, without continuity solutions.
2. Level 1: Microorganisms with a low degree of DNA damage DNA: the nucleoid appears compact, but with discrete peripheral fragments with a relatively large size, after DNA breakages.
3. Level 2: Microorganisms with a medium degree of DNA damage: the nucleoid is more relaxed, occupying a larger surface, with discrete peripheral fragments with a relatively large size, after DNA breakages.
4. Level 3: Microorganisms with a high degree of DNA damage: the nucleoid appears much more relaxed and extended, with a larger number of peripheral fragments, after DNA breakages,
5. Level 4: Microorganisms with massively fragmented DNA: they show a wide and diffuse halo of more or less punctiform DNA fragments which have diffused according to a gradient in the agarose matrix.

The criterion for establishing the correlation between the size of the halos due to fragment diffusion and DNA fragmentation is derived from the results obtained using the DBD-FISH technique (Fernández J L, Goyanes V J, Ramiro-Diaz J, Gosálvez J. Application of FISH for in situ detection and quantification of DNA breakage. Cytogenet Cell Genet. 1998; 82:251-256: Fernández J L, Vázquez-Gundín F, Delgado A, Goyanes V J, Ramiro-Diaz J, de la Torre J. Gosálvez J. DNA breakage detection-FISH (DBD-FISH) in human spermatozoa: technical variants evidence different structural features. Mutat Res 2000; 453:77-82; Fernández J L, Gosálvez J. Application of FISH to detect DNA damage: DNA Breakage Detection-FISH (DBD-FISH). Methods Mol Biol 2002; 203:203-216; Fernández J L, Goyanes V, Gosálvez J. DNA Breakage Detection-FISH (DBD-FISH). In: Rautenstrauss B, Liehr T, eds. FISH technology-Springer lab manual. Heidelberg: Springer-Verlag; 2002; 282-290)

This process allows detecting and quantifying the DNA breakages in deproteinized cell nuclei subjected to controlled DNA denaturation. This denaturation generates single-stranded DNA sections from the breakage ends, which are detected by means of in situ hybridization using a total genomic DNA probe labeled with a fluorochrome, visible by means of fluorescence microscopy. The greater the breakage level in cell DNA, the larger is the amount of single-stranded DNA generated by the denaturing solution, the larger is the amount of hybridized probe and the greater is the fluorescence observed. The samples processed according to the methodology described in the present invention were exposed, after lysis, to an alkaline denaturing solution for 2.5 minutes a 22° C. This solution generates single-stranded DNA sections from the breakage ends existing in the DNA. Therefore, the hybridization intensity using a total genomic DNA probe will be related to the amount of breakages present in the bacterial DNA. It has thus been confirmed that relaxed nucleoids with fragments show intense labeling with DBD-FISH, which demonstrates the intense fragmentation of their DNA (Example 1 and FIG. 3). The remaining nucleoids show very low labeling levels with this probe, corresponding to the hybridization background generated by the actual treatment of the nucleoid.

The described protocol is effective in most Gram-negative bacteria. In said bacteria, the lysis solution is enough to lyse the cell wall and observe the entire bacterial chromosome and DNA fragment diffusion in the event of fragmentation of such DNA. To analyze bacteria with a resistant wall, such as Gram-positive bacteria, it is necessary to incubate them in suspension with lytic wall enzymes prior to the inclusion in the microgel. For example, staphylococci must be resuspended with lysostaphin (20 micrograms/ml) in Tris-EDTA (TE) buffer. Enterococci must be incubated with a mixture of lysozyme (2 mg/ml) and mutanolysin (50 micrograms/ml) in Tris-EDTA (TE) buffer. Yeast cells are incubated in a buffer containing 1M sorbitol, 0.1M EDTA, 15 mM beta-mercaptoethanol, pH 7.5, and Zymolase (200 U/ml), Lyticase or Glucalase (Ligozzi M, Fontana R. Isolation of total DNA from bacteria and yeast. Afr J Biotech 2003; 2: 251-253).

The incubations must be carried out for at least 5-30 minutes at 37° C., and the microorganism solution must be mixed with the low melting point agarose to be included in a microgel. There are other enzymes which for the moment are not so common but can be effective for lysing Gram-positive bacteria, such as achromopeptidase and especially labiase (Niwa T, Kawamura Y, Katagin Y, Ezaki T. Lytic enzyme, labiase for a broad range of Gram-positive bacteria and its application to analyze functional DNA/RNA, J. Microbial Methods 2005; 61:251-260).

Another possibility is to incubate with lysozyme (5 mg/ml) and 24% polyethylene glycol 20,000 for 2 hours at 37° C. (Maassen C B M. A rapid and safe plasmid isolation method for efficient engineering of recombinant lactobacilli expressing immunogenic or tolerogenic epitopes for oral administration. J Immunol Method 1090:223:131-136.). The gel lysis could be alkaline. The use of organic solvents (acetone, butanol, toluene, etc.) can also aid in breaking up the bacterial wall (Harrison S T L. Bacterial cell disruption: a key unit operation in the recovery of intracellular products. Biotech Adv 1991; 9:217-240.). The use of mechanical systems for breaking the cell wall by means of sonication or stirring with disrupting particles are not recommendable because they can damage the DNA of the microorganism.

The present invention also contemplates a kit for assessing DNA fragmentation in microorganisms. This kit contains a lysis solution and a fluorochrome. The kit also contains the support pretreated with agarose, for example, as well as a solution for preparing a medium with similar features to those of a suspension which will contain the sample, for example, a low melting point agarose solution which allows preparing a microgel.

The content and mode of use of a kit according to an embodiment of the invention are detailed below.

Description of the Content of the Kit

Pretreated slides*

Eppendorf tubes containing 140 microliters of 1% low melting point agarose in distilled water or PBS, gelled Tubes with lysis solution*. Composition: 0.01M Tris, 0.05M EDTA, 0.1M DTT, 2% SDS, pH 10 (adjusted with NaOH).

Fluorochrome

Vessel with lid for horizontal incubation with the lysis solution

Lancet

Floats for Eppendorf tubes

* Prepared as mentioned in the description

Required Material and Equipment

Fluorescence microscope (immersion lens recommendable)
Refrigerator at 4° C.
Drying oven at 37° C.
Drying oven or plate at 80° C. (optional)
Incubation bath at 37° C.
Plastic gloves
Glass covers slip (18×16 mm, 22×22 mm or 24×60 mm)
Micropipettes
4 boxes for horizontal incubations
Distilled water
70%, 90%, 100% ethanol
Instructions for Use
Preparation of a sample per slide:
1) Place lysis solution in a covered horizontal incubation vessel in a drying oven at 37° C.
2) Dilute the microorganism sample in culture medium or PBS at a concentration of 5-15 million per milliliter.
Preparation of the Agarose Microgel
3) Introduce the Eppendorf tube with gelled agarose in the float, leaving it at the lid level, and leave it to float for 5 minutes in water at 90-100° C. until the agarose melts. The agarose can alternatively be melted in a microwave oven.
4) Transfer the Eppendorf tube with the float to a thermostatic bath at 37° C. and leave for 5 minutes until the temperature is balanced.
7) Add 60 microliters of the microorganism sample to the content of the Eppendorf tube and resuspend, using the micropipette.
8) Place a pretreated slide on a cold surface at 4° C. (for example, a metal or glass sheet).
9) Once the slide has cooled, deposit the microorganism suspension with agarose and place a glass cover slip, preventing the formation of air bubbles. Depositing a drop of 12, 20 or 50 microliters is recommended for a cover slip of 18×18 mm, 22×22 mm or 24×60 mm, respectively.
10) Introduce the cold sheet with the slide in the refrigerator and allow the sample to gel for 5 minutes.
Processing the Samples
11) Using gloves, remove the cover slip by sliding it gently and immediately introduce the slide horizontally in the vessel with the lysis solution, covering and allowing to incubate for 5 minutes in the drying oven or bath at 37° C.
12) Lift the slide with the aid of the lancet using gloves. Hold it horizontally and deposit it horizontally in a box containing abundant distilled water or buffer solution to wash the lysis solution. Allow to incubate for 5 minutes.
13) Introduce the slide horizontally in a box with 70% ethanol (5 minutes), then in another box with 90% ethanol (5 minutes), and finally in 100% ethanol (5 minutes), a −20° C.
14) Allow to air dry, and incubate in a microwave oven at 500-1000 W for 3-10 minutes, or by default, in a drying oven at 80° C. for at least one hour or overnight. Once dry, the processed slides can be stored in filing boxes at room temperature, in the dark, for months.
Staining the Samples for Observation Under a Fluorescence Microscope
Depending on the availability of fluorescence filters, the samples can be stained with DNA-specific fluorochromes of the EvaGreen (green) or GelRed (red) type. The fluorochromes of the SYBR family, specifically SYBR Gold, allow good resolution with certain photostability.
Storage and Stability
Store at room temperature.
Shelf-life: the reagents and materials are stable for a period of at least 6 months. It is recommended that the lysis solution is maintained in a vertical position and well closed. The examples set forth below are described as a support for particular aspects of the invention, and in no case do they limit the scope thereof.

Example 1

Confirmation of the Presence of DNA Breakages in the Nucleoids Showing Fragment Diffusion The described methodology was applied in a sample of *Escherichia coli* strain TG1 in an exponential growth phase in LB medium at 37° C. in order to produce DNA segment diffusion halos spontaneously in those with fragmented DNA. To that end, the sample diluted to a concentration of 10-20 million per milliliter in PBS or LB medium was mixed with 1% low melting point liquid agarose in order to obtain a final concentration of the latter of 0.7%. After gelling the microgel on the slide, the sample was incubated in the lysis solution formed by 0.01M Tris, 0.05M EDTA, 0.1M DTT, 2% SDS, pH 10 (adjusted with NaOH) for 5 minutes at 37° C. The slides were washed in physiological saline for 5 minutes. DBD-FISH (DNA Breakage Detection-Fluorescence in Situ Hybridization; Fernández at al., 1998; 2000; 2002; Fernández and Gosálvez, 2002) was subsequently formed sequentially on the actual cells using a total genomic *Escherichia coli* DNA probe. This process allows detecting and quantifying DNA breakages in the nuclei of cells immersed in agarose microgels that are deproteinized and subjected to controlled DNA denaturation. This denaturation generates single-stranded DNA sections from the breakage ends, which are detected by means of in situ hybridization using a total genomic *Escherichia coli* DNA probe labeled with a fluorochrome emitting red fluorescence (Cy3). The greater the breakage level in the DNA, the larger is the amount of single-stranded DNA generated by the denaturing solution, the larger is the amount of the hybridized probe and the greater is the red fluorescence obtained. According to the process of the present invention, the processed samples contain single-stranded DNA generated by the denaturing solution from possible breakage ends existing in the DNA. The hybridization intensity using a total genomic DNA probe will therefore be related to the amount of breakages present in the *Escherichia coli* nucleoid.

250 randomly obtained cells were counted. The DAPI staining images of the chromatin dispersion halos were captured by using a cooled CCD camera using two filters for the simultaneous viewing of the dispersion halos, visible in blue, and of the hybridization signal, visible in red. The purpose was to confirm that the nucleoids with DNA fragment diffusion have breakages of such DNA. The results demonstrated that the nucleoids with DNA fragment diffusion have a high labeling intensity of the DNA breakages by means of DBD-FISH (FIG. 3).

As a result, the simple determination of DNA fragment diffusion, such fragments being obtained by means of the present process, offers a simple and direct estimation of DNA fragmentation.

Example 2

Evaluation of Spontaneous DNA Fragmentation in Different Bacterial Species

Nine bacterial species growing in a plate were taken and the frequency of bacteria with DNA fragmentation in said samples was determined. The following bacterial species were processed: *Escherichia coli, Enterobacter cloacae,*

Pseudomonas aeruginosa, Proteus mitabilis, Salmonella spp., Stenotrophomonas maltophilia, Acinetobacter baumannii, Klebsiella oxytoca, Kiebsiella pneumoniae.

Each sample was incubated in an agarose microgel, three 18×18 mm microgels being carried out in each slide, each one corresponding to a different species. One of the microgels of each slide corresponded to the same *Escherichia coli* culture, as a result and processing control. The slides were incubated in the lysis solution, washed, dehydrated, and allowed to dry at 80° C. for 3 hours, stained with SYBR Gold and examined with the fluorescence microscope. One thousand cells per bacterial species were counted. The results are shown in Table 1. The lysis was effective for obtaining nucleoids in all the analyzed species (FIG. 4). Cells with nucleoids the DNA of which was massively fragmented (level 4), diffusing in the agarose matrix, were also observed in all the species. This fragmentation occurred in a spontaneous, basal manner in the culture and was not induced by any agent, its frequency varying from one culture to another.

TABLE 1

Distribution of the percentages of cells with fragmented DNA in 6 bacterial species.

| Microorganism | DNA Fragmentation |
|---|---|
| *Escherichia coli* | 5.24 |
| *Proteus mirabilis* | 5.91 |
| *Acinetobacter baumannii* | 39.59 |
| *Pseudomonas aeruginosa* | 3.35 |
| *Salmonella* spp. | 5 |
| *Stenotrophomonas maltophilia* | 6.29 |

Example 3

Evaluation of DNA Fragmentation after Incubation with Different Antimicrobial Agents. Damage Due to Exogenous Agents As an illustrative example, a study is set forth attempting to determine the possible DNA damage induced by three antibiotics: ampicillin, gentamicin and ciprofloxacin, and a hydroxyl radical generating agent, hydrogen peroxide ($H_2O_2$), applied on cultures of *Escherichia coli* strain TG1, which is sensitive to all of them, growing in exponential phase in LB medium. The agents used have different antimicrobial action mechanisms. Ampicillin is a beta-lactam antibiotic affecting cell wall peptidoglycan synthesis after binding to PBPs (penicillin binding proteins) and activating autolysins. Gentamicin is an aminoglycoside antibiotic affecting protein synthesis at the level of the 30S subunit, binding to protein p10 of bacterial ribosomes. Ciprofloxacin is an antibiotic of the quinolone family, inducing DNA double-strand breakages as a result of inhibiting DNA gyrase and topoisomerase IV. The agents were mixed on the liquid LB culture medium at the concentrations and incubation times specified in Table 2. After said incubation times, the bacteria were processed according to the process of the present invention to determine the percentage of bacteria with fragmented DNA.

Simultaneously, another aliquot thereof was incubated with a vital stain. This is a dye exclusion test, using a green fluorochrome (SYBR Green II) binding to DNA and penetrating all the cells, mixed with a red fluorochrome, propidium iodide (PI), which only penetrates the cells with deficient membrane functionalism, presumably "dead" cells "Live" cells are thus stained green since they exclude the red dye, whereas "dead" cells cannot expel the red dye and are stained with PI. The results are shown in Table 2. After studying 5,000 bacteria at each experimental point, it was observed that gentamicin, ciprofloxacin and hydrogen peroxide only induced a very discrete increase of cells with a membrane permeable to PI, whereas said increase was spectacular with ampicillin. But ampicillin hardly increased the percentage of cells with fragmented DNA, gentamicin. However, ciprofloxacin and $H_2O_2$ at high doses induced massive DNA fragmentation of all the examined cells (level 4, FIG. 5). This result demonstrates that the assessment of membrane permeability is not a universal parameter as a vitality indicator and that the study of DNA can provide supplementary valuable information which is not provided by said staining and vice versa.

TABLE 2

Percentages of *Escherichia coli* bacteria stained by the vital stain and percentage of bacteria with fragmented DNA after the action of different antimicrobial agents.

| Agent | Vital Stain | | DNA Fragmentation |
|---|---|---|---|
| | Permeable | Empty Capsules | |
| Control | 0.50 | 0.05 | 0.30 |
| Ampicillin [300 µg/ml] (40 min) | 50.00 | 5.00 | 4.20 |
| Gentamicin [300 µg/ml] (40 min) | 10.00 | 0.50 | 3.70 |
| Ciprofloxacin [25 µg/ml] (40 min) | 5.00 | 0.30 | 100.00 |
| $H_2O_2$ [10 mM] (10 min) | 5.00 | 0.30 | 100.00 |

Example 4

Evaluation of the Sensitivity or Resistance of a Microorganism to a Certain Agent A study is shown of the effect of ciprofloxacin at DNA level in an *Escherichia coli* strain sensitive (TG1) to and in another strain resistant to this antibiotic, growing in exponential phase.

The mean inhibitory concentration (MIC) of growth was 0.012 micrograms/ml. In contrast, the growth of the resistant strain was not affected by the maximum concentration used in the commercial test (MIC>32 micrograms/ml). Six concentrations of ciprofloxacin applied to cultures in LB medium for 40 minutes were studied, and the vital stain study was conducted in a manner similar to that described in the previous example (Table 3), and the DNA damage level was studied according to the protocol of the invention. In the sensitive strain, a very discrete increase of cells permeable to PI and with an empty capsule was shown as the antibiotic dose was increased at the level of the highest doses used. The vital stain did not detect any effect in the resistant strain.

TABLE 3

Percentages of *Escherichia coli* bacteria stained by the vital stain after the exposure to increasing ciprofloxacin doses in a strain sensitive to another strain resistant to the antibiotic.

| | Vital Stain | | | |
| --- | --- | --- | --- | --- |
| | Sensitive Strain | | Resistant Strain | |
| Ciprofloxacin Dose | Permeable | Empty Capsules | Permeable | Empty Capsules |
| Control (0.00 µg/ml) | 0.40 | 0.00 | 0.66 | 0.03 |
| 0.50 µg/ml | 0.95 | 0.05 | 0.65 | 0.00 |
| 1.00 µg/ml | 1.04 | 0.00 | 0.72 | 0.10 |
| 2.50 µg/ml | 2.60 | 0.15 | 0.87 | 0.10 |
| 5.00 µg/ml | 2.67 | 0.24 | 1.08 | 0.10 |
| 10.00 µg/ml | 3.60 | 0.48 | 0.82 | 0.15 |

Figure 2:
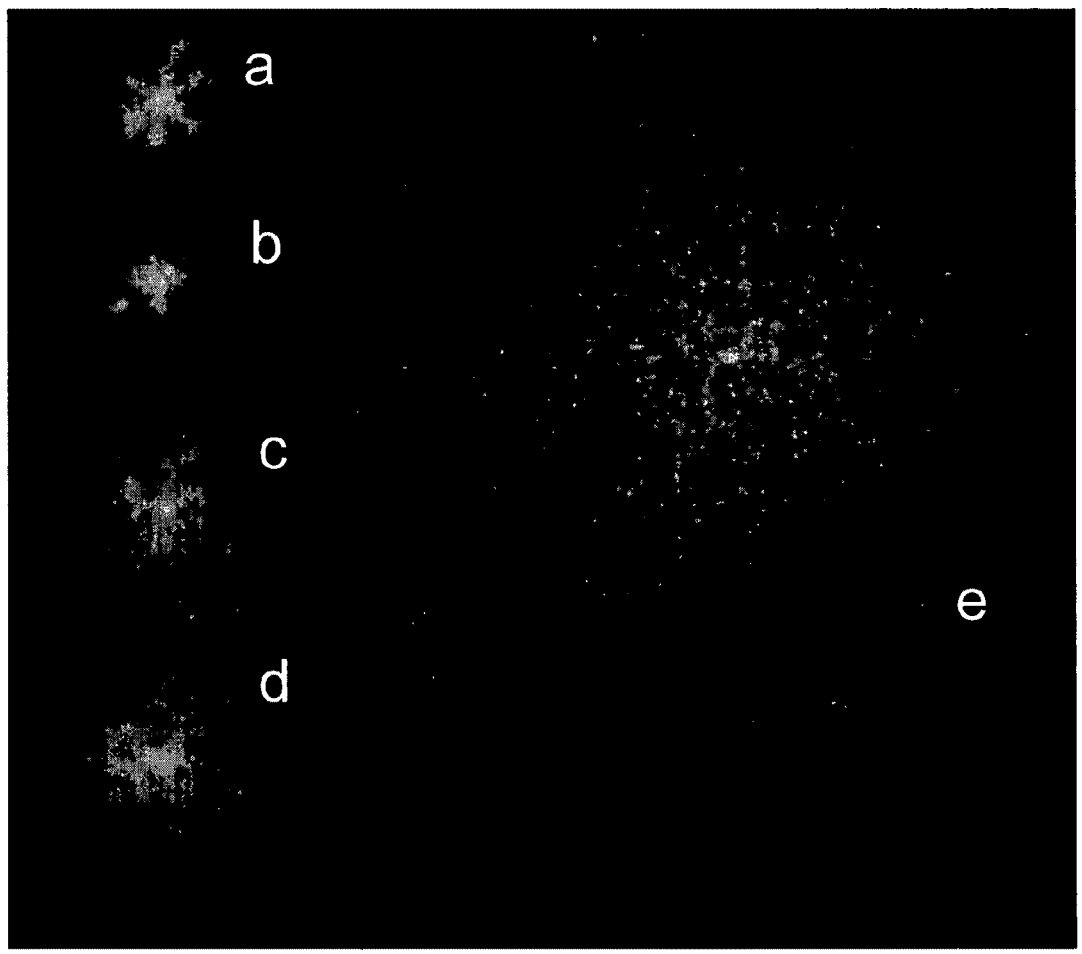
FIG. 2 shows different progressive degrees of *Escherichia coli* DNA damage.

The damage at DNA level was observed in the sensitive strain and at the lowest concentration used in the experiment (0.5 µg/m). Furthermore, with this concentration, the damage level corresponded to type 4, i.e. the maximum in the previously established scale (FIG. 2). All these microorganisms showed massively fragmented DNA, with a wide and diffuse halo of punctiform DNA fragments which have diffused in the agarose matrix according to a gradient from the central area of the nucleoid. Doses greater than 0.5 µg/ml did not seem to modify the fragmentation images, a slightly greater diffusion perhaps being observed, especially in the central area of the nucleoid. This could indicate a close-to-saturation effect of DNA damage due to ciprofloxacin.

Example 5

Determination of the Possible Effect of Low Ciprofloxacin Doses, Close to MIC, on DNA Integrity Once it has been determined that ciprofloxacin at high concentrations induces massive DNA fragmentation, it is interesting to determine whether the technique can discriminate any effect at the level of DNA integrity after the exposure of the sensitive *Escherichia coli* strain (TG1) to low concentrations of the antibiotic above, below and at the MIC level (0.012 micrograms/ml). The doses used are shown in Table 4, the incubation time being 40 minutes in exponential growth phase in LB medium. Table 4 shows the results of the vital stain. Although there is a tendency to increase the percentage of cells permeable to PI and with an empty capsule as the dose is increased, this is not significant with the low doses used,

TABLE 4

Percentages of *Escherichia coli* bacteria stained by the vital stain after the exposure to increasing low ciprofloxacin doses in a sensitive strain.

| | Vital Stain Sensitive Strain | |
| --- | --- | --- |
| Ciprofloxacin Dose | Permeable | Empty Capsules |
| Control (0.00 µg/ml) | 1.30 | 0.60 |
| 0.003 µg/ml | 1.50 | 0.70 |
| 0.006 µg/ml | 2.10 | 0.76 |
| 0.012 µg/ml | 2.30 | 1.06 |
| 0.100 µg/ml | 2.40 | 1.40 |

The DNA damage level was determined by means of the process object of the present invention. The highest dose (0.1 micrograms/ml), above the MIC, showed damage in all the cells analyzed. Such damage tended to be homogeneous among the different cells, having a lower magnitude than the massive crushing described in the previous example, with doses of 0.5 micrograms/ml and above. However, the degree of damage was considerable, similar to level 3 (FIG. 2). This level is qualified as a high degree of DNA damage. The nucleoid appears very relaxed and extended, with a large number of peripheral fragments after DNA breakages.

The dose similar to the MIC also caused clear and homogeneous damage among the different nucleoids, but with a magnitude similar to level 2 of the scale (FIG. 2). It corresponds to a medium degree of DNA damage. The nucleoid appears relaxed, occupying a larger surface than in the control without treatment, with discrete peripheral fragments with a relatively large size, after DNA breakages.

The dose of 0.006 micrograms/ml, half the MIC, also induced clear and homogeneous damage among the different nucleoids, its magnitude being intermediate between level 1 and 2 in the arbitrary damage scale (FIG. 2).

Finally, the dose of 0.003 micrograms/ml, a third of the MIC, also induced evident damage but at level 1. This corresponds to a low degree of DNA damage DNA, where the nucleoid appears compact, but with discrete peripheral fragments with a relatively large size, after DNA breakages (FIG. 2).

In conclusion, the process object of the present invention has a high resolution, such that damage induced by very low concentrations of ciprofloxacin, below the MIC, which do not significantly inhibit bacterial growth nor affect the "viability" determined by the vital stain can even be detected. It is possible that the low damage levels can be repaired by the enzymatic DNA repair machinery, allowing cell viability.

Example 6

Determination of the Minimum Incubation Time with Ciprofloxacin which Allows Detecting DNA Damage in the Sensitive *Escherichia coli* Strain

*Escherichia coli* strain TG1 in exponential growth in LB medium was incubated during decreasing time periods: 40 minutes, 15 minutes, 5 minutes, 2.5 minutes and 0 minutes, with a dose of 1 microgram/ml of ciprofloxacin. A ciprofloxacin-free control was also included. The average time necessary for the inclusion in a microgel and cooling in a refrigerator was estimated at 1.5 minutes. It can be presumed that the antibiotic is working during this time, therefore the time of 1.5 minutes should be added to each of the assayed times.

After 40 minutes, all the bacteria showed massively crushed DNA (level 4: FIG. 6). An effect was also demonstrated with a time of 15 minutes. In this case, the damage also tended to be homogeneous among the different nucleoids, but having a much lower magnitude of a medium degree (level 2) (FIG. 6). The minimum time in which evident DNA damage was detected was 5 minutes, being a low degree of damage (level 1), although with 2.5 minutes a slight increase in nucleoid relaxation seemed to be viewed compared to that of 0 minutes and to the control, but it was difficult to assess.

As a result, the technique object of the invention allows recognizing that the DNA damage caused by a lethal ciprofloxacin dose is accumulative over time and is not instantaneous or generated in a relatively short time period. The minimum time of incubation to detect a minimal effect at DNA level using a dose of 1 microgram/ml was 5 minutes+ 1.5 minutes=6.5 minutes.

Example 7

Viewing DNA Damage after the Culture with Antibiotics that do not Act at DNA Level, Incubating for 24 Hours The purpose is to observe if, despite not seeing damage initially at the DNA level, cell death means late fragmentation of such DNA. To that end, *Escherichia coli* strain TG1, growing in exponential phase in liquid LB medium, was incubated for 24 hours with ampicillin (300 micrograms/ml). This beta-lactam antibiotic affects cell wall peptidoglycan synthesis after binding to PBPs (penicillin binding proteins) and activating autolysins. For the comparison, an aliquot of the culture was processed after 40 minutes of treatment, both for the vital stain and for determining DNA damage by means of the technique of the invention. Table 5 shows the data of the vital stain. After 20 minutes of incubation with the beta-lactam antibiotic, the percentage of cells with an altered wall, permeable or with an empty capsule appearance clearly increased. After one day of incubation, the increase was spectacular, especially the cells with an empty capsule appearance, almost all of them appearing dead from the point of view of the vital stain.

TABLE 5

Percentages of *Escherichia coli* bacteria stained by means of the vital stain after incubation with ampicillin.

| | Vital Stain | | | |
|---|---|---|---|---|
| | 20 minutes. | | 24 hours | |
| Agent | Permeable | Empty Capsules | Permeable | Empty Capsules |
| Control | 0.32 | 0.20 | 0.90 | 25.10 |
| Ampicillin | 5.22 | 0.67 | 17.29 | 75.97 |

The determination of DNA damage according to the technique of the invention demonstrated that differences were not observed with respect to the control after 20 minutes of incubation. However, after 24 hours there was little density of nucleoids and they showed a relaxed appearance, without a well defined central area. What was most striking was the massive presence of punctiform degraded DNA fragments homogeneously distributed over the bottom of the preparation (FIG. 7). The process object of the present invention demonstrates that cell death, although it is not initially due to direct DNA damage, can indirectly lead to massive DNA damage over time.

Example 8

Viewing the Evolution of DNA Damage Generated by Ciprofloxacin in a Sensitive *Escherichia coli* Strain. Application of Digital Image Analysis Systems for Evaluating Damage

*Escherichia coli* strain TG1, in exponential growth in 400 microliters of LB medium, was incubated with 10 micrograms/ml ciprofloxacin for 40 minutes. The bacteria were subsequently centrifuged and resuspended in 400 microliters of ciprofloxacin-free medium. This operation was repeated again to wash the antibiotic. The bacteria were incubated 0, 15, 30, 60 and 90 minutes, after which they were processed according to the process of the invention. A control without antibiotic treatment was simultaneously processes in the same slide in each time.

After the staining with SYBR Gold, the images were captured with a high-sensitivity cooled CCD KX32ME camera (Apogee Instruments, Roseville, Calif.). The images were subsequently analyzed by means of a macro designed with the Visilog 5.1 program (Noesis, France). This allowed the segmentation and correction of the bottom and luminosity differences in the field. The results of the total surface of the bacterial staining, of the area of the residual capsule, and of the halo of dispersed DNA loops or fragments (total area-area of the capsule), in pixels, were transcribed to an Excel table. Finally, a statistical study of said data was conducted by means of the SPSS 12.5 program using the non-parametric Mann-Whitney U test and Kruskal-Wallis H test ($p<0.05$).

The results demonstrated that double-stranded DNA breakages caused by ciprofloxacin can be repaired if the antibiotic is eliminated from the medium. Immediately after the treatment, high fragmentation (level 3-4) can be seen. A decrease in the surface of the fragment diffusion halo begins to be detected in a statistically significant manner after 15 minutes, such fragments having a larger size. This halo continues to decrease more slowly during 30 and 60 minutes, showing increasingly fewer fragments, decreasing significantly, more widely, after 90 minutes. (FIG. 6A). In this case, fragments are no longer detected but rather DNA relaxation loops are without differences with respect to the controls without treatment (level 0). DNA breakage repair kinetics has thus been obtained, such DNA being completely repaired in appearance after 90 minutes of incubation. However, this does not mean that the repair has always been correct. Curiously enough, the size of the bacterial capsules increases about double, on average, after the final times of 60 and 90 minutes, with respect to the rest of the assayed times (FIG. 8B). This increase is irregular and heterogeneous among the different bacteria.

The process object of the present invention demonstrates a highly clinically important fact, i.e. the importance of maintaining the correct antibiotic doses for prolonged times. If such antibiotic is withdrawn prematurely, the damage initially caused in the bacterium can be reverted.

Example 9

Development of Software for the Automated Measurement of DNA Fragmentation Levels Using the methodology contemplated in Example 6 of the present invention, a basic methodology has been designed fixing the basis for the morphological characterization of the images generated by bacteria having fragmented DNA and non-fragmented DNA using conventional image analysis systems. The process allows discriminating between both types of bacteria automatically and therefore objectively.

The overall process comprises the design of two strategies: 1) a model for interactively capturing images and making decisions based on the number of elements analyzed (FIG. 9). 2) a segmentation routine for selecting the ROIs (Regions Of Interest) (FIG. 10).

In this practical example, direct capture under a fluorescence microscope (×100) was used, using a cooled monochrome COD camera with a 12-bit color depth. The images were saved as .tiff and were processed using the public domain Scion Image program (NIH IMAGE USA). This program contains the minimum tools necessary for performing segmentation operations and can measure integrated fluorescence densities in the images that are processed. The integrated density relates the sum of the different gray levels in the AOI with the area by carrying out a subtraction of the background. Using this tool, 9 series of experiments were processed in which 100 bacteria containing non-fragmented DNA and 100 bacteria with fragmented DNA were captured. The results show that very similar values are generated between each of the series when the grouping and comparison criterion is: bacteria having fragmented DNA versus bacteria that do not have fragmented DNA.

It is therefore possible to discriminate the two types of states of bacterial DNA based on objective observations carried out based on image analysis environments.

Although only fluorescence areas and the intensities of the selected areas have been measured in this case, there are other criteria in relation to the textures generated by each type of image, therefore both populations could be characterized and discriminated.

We claim:

1. A kit for assessing DNA fragmentation in a bacteria, comprising:
    pretreated slides;
    an agarose solution;
    a lysis solution including:
        a chelating agent;
        a reducing agent;
        a buffer; and
        an ionic protein denaturing detergent, said ionic protein denaturing detergent being the only detergent in said kit, said ionic protein denaturing detergent present in an amount effective to lyse said bacteria at a pH of between 6.5 and 10.5 to obtain said DNA nucleoid of said bacteria; and
    a fluorochrome.

2. The kit according to claim 1, wherein said reducing agent comprises between 0.001M and 2 M dithiothreitol, and wherein said buffer comprises between 0.001 M and about 2M 2-amino-2(hydroxymethyl)-1,3-propanediol, and wherein said chelating agent comprises between about 0.001M and about 2M ethylenediaminetetraacetic acid, and wherein said ionic protein denaturing detergent comprises between about 0.1% and about 3% sodium dodecyl sulfate.

3. The kit according to claim 2, wherein said lysis solution is adjusted to a pH between 6.5 and 10.5.

4. The kit according to claim 1, wherein said reducing agent comprises 0.1M dithiothreitol, and wherein said buffer comprises 0.01M 2-amino-2(hydroxymethyl)-1,3-propanediol, and wherein said chelating agent comprises 0.05M ethylenediaminetetraacetic acid, and wherein said ionic protein denaturing detergent comprises 2% sodium dodecyl sulfate.

5. The kit according to claim 2, wherein said reducing agent comprises 0.1 M dithiothreitol, and wherein said buffer comprises 0.01 M 2-amino-2(hydroxymethyl)-1,3-propanediol, and wherein said chelating agent comprises 0.05M ethylenediaminetetraacetic acid, and wherein said ionic protein denaturing detergent comprises 2% sodium dodecyl sulfate.

6. The kit according to claim 1, wherein the lysis solution is adjusted to a pH of about 10 with NaOH.

7. The kit according to claim 2, wherein the lysis solution is adjusted to a pH of about 10 with NaOH.

8. The kit according to claim 1, wherein said fluorochrome is sufficiently sensitive to enable detection of DNA fiber of nucleoids of said bacteria.

9. The kit according to claim 1, where said fluorochrome is selected from the group consisting of: GelRed, 10 EvaGreen, SY8R, PicoGreen, TOTO, YOYO, 8080, POPO, JOJO, LOLO, SYTOX, POPRO, 80-PRO, YO-PRO, TO-PRO, JO-PRO, PO-PRO, LO-PRO, and combinations thereof.

10. The kit according to claim 1, wherein said pretreated slides further comprise an agarose film.

11. The kit according to claim 1, wherein said agarose solution comprises a low melting point agarose.

12. The kit according to claim 1, wherein said agarose solution comprises between about 0.3% and 1% agarose.

13. The kit according to claim 1, wherein said lysis solution further comprises a pH of 10.

14. The kit according to claim 1, wherein said pretreated slides comprise glass slides for supporting and retaining a microgel containing said bacteria.

15. The kit according to claim 1, wherein said agarose solution comprises an inert microgel.

16. The kit according to claim 1, wherein said ionic protein denaturing detergent is present in an amount effective to extract bacteria cell walls, membranes and proteins.

17. The kit according to claim 1, wherein said fluorochrome comprises a DNA specific fluorochrome.

* * * * *